(12) United States Patent
Hsiao

(10) Patent No.: US 11,421,840 B1
(45) Date of Patent: Aug. 23, 2022

(54) AROMA DIFFUSER THAT SIMULATES THE AURORA

(71) Applicant: DONGGUAN YIH TEH ELECTRIC PRODUCTS CO., LTD., Dongguan (CN)

(72) Inventor: Ming Jen Hsiao, Miaoli County (TW)

(73) Assignee: DONGGUAN YIH TEH ELECTRIC PRODUCTS CO., LTD., Guangdong (CN)

( * ) Notice: Subject to any disclaimer, the term of this patent is extended or adjusted under 35 U.S.C. 154(b) by 0 days.

(21) Appl. No.: 17/570,325

(22) Filed: Jan. 6, 2022

(51) Int. Cl.
  *F21S 10/02* (2006.01)
  *A61L 9/03* (2006.01)
  *F21V 33/00* (2006.01)
  *F21V 1/10* (2006.01)
  *F21Y 115/10* (2016.01)

(52) U.S. Cl.
  CPC ............... *F21S 10/02* (2013.01); *A61L 9/03* (2013.01); *F21V 1/10* (2013.01); *F21V 33/004* (2013.01); *A61L 2209/12* (2013.01); *F21Y 2115/10* (2016.08)

(58) Field of Classification Search
  CPC .... F21S 10/02; A61L 9/03; F21V 1/10; F21V 33/004
  USPC ........................................................ 362/231
  See application file for complete search history.

(56) References Cited

U.S. PATENT DOCUMENTS

| | | | |
|---|---|---|---|
| 7,963,460 B2 | 6/2011 | Hsiao | |
| 7,992,801 B2 | 8/2011 | Hsiao | |
| 8,029,153 B2 | 10/2011 | Hsiao | |
| 8,133,440 B2 | 3/2012 | Hsiao | |
| 8,196,903 B2 | 6/2012 | Hsiao | |
| 8,201,957 B2 | 6/2012 | Hsiao | |
| 8,765,073 B1 | 7/2014 | Hsiao | |
| 8,983,277 B2 | 3/2015 | Hsiao | |
| 9,206,963 B2 * | 12/2015 | Hsiao | ...................... F21V 15/00 |
| 9,410,695 B2 | 8/2016 | Hsiao | |
| 9,500,358 B2 | 11/2016 | Hsiao | |
| 10,064,969 B2 | 9/2018 | Hsiao | |
| 2014/0014736 A1 * | 1/2014 | Wirz | ........................ A61L 9/03 239/135 |
| 2015/0109823 A1 * | 4/2015 | Hsiao | ........................ A61L 9/02 362/643 |
| 2015/0117056 A1 * | 4/2015 | Hsiao | ........................ A61L 9/03 362/611 |
| 2016/0195257 A1 * | 7/2016 | Hsiao | .................. F21V 33/0004 362/92 |

(Continued)

*Primary Examiner* — Bryon T Gyllstrom
(74) *Attorney, Agent, or Firm* — Sinorica LLC

(57) ABSTRACT

An aroma diffuser equipped with an aurora-like situation to release fragrance, and an illuminator of a light-emitting device is used to radiate a light source to a rotating aurora reflector to reflect or diffuse or refract to produce light similar to the aurora effect. The rotating aurora reflector can rotatably reflect or diffusely reflect the radiation source of the illuminator to produce the constant changes of the aurora, and constantly change the diffuse light spot or arc-shaped ray arc. The aurora colors provided by the light-emitting device, such as green, red, or mixed colors, are reflected in a tubular light-transmitting lampshade and its outer light-transmitting shell to produce aurora scene lighting decoration or lighting effects to match the aforementioned aromatic scent atmosphere.

20 Claims, 6 Drawing Sheets

(56) References Cited

U.S. PATENT DOCUMENTS

| | | | |
|---|---|---|---|
| 2016/0375169 A1* | 12/2016 | Hsiao | F21V 33/0028 |
| | | | 362/92 |
| 2017/0136138 A1* | 5/2017 | Ma | A61L 9/12 |
| 2017/0136260 A1* | 5/2017 | Campos | A61K 45/06 |
| 2018/0126022 A1* | 5/2018 | Hsiao | A61L 9/013 |
| 2019/0022267 A1* | 1/2019 | Hsiao | A61L 9/03 |
| 2019/0022268 A1 | 1/2019 | Hsiao | |

\* cited by examiner

AROMA DIFFUSER THAT SIMULATES THE AURORA

BACKGROUND OF THE INVENTION

1. Field of the Invention

The present invention relates to scent releasing devices and more specifically, to an aroma diffuser equipped with light decoration changes to simulate the aurora.

2. Description of the Related Art

People have a mysterious interest in aurora. Travelers see an aurora that has never been seen before near the poles, and they have inexplicable joy and imagination, because it has a diffuse glow or arc light or curtain of various mixed colors such as unusual green or red. This is due to a large-scale electrical discharge process around the earth. The magnetic field of charged particles from the sun near the earth forces some of them to follow the magnetic field lines to the north and south poles, and collide with atoms and molecules in the atmosphere to excite the northern lights or southern lights that produce various shapes of light. Many times when the aurora appears, it presents a diffuse glow or curtain-like parallel light. Sometimes it forms a static arc, while other active aurora is constantly changing, constantly changing its shape.

Known aroma diffusers, such as the luminous decorations of U.S. Pat. Nos. 10,60,3399, 10,59,6293, and 10,413,629 patents, fail to provide ambient effects such as diffuse luminescence of various mixed colors of aurora rays or arc rays. They have the problem of not being able to produce better light effects and aromatic environmental atmosphere.

SUMMARY OF THE INVENTION

The present invention has been accomplished under the circumstances in view. It is therefore an object of the present invention to provide an aroma diffuse that simulates the aurora. The aroma diffuser of the present invention comprises a light-transmitting shell, a heat transfer unit, a heating element, a base, a light-emitting device, and a rotating aurora reflector. The light-transmitting shell is a hollow shell in the embodiment. The light-transmitting shell comprises a first opening located on one side thereof, and a second opening located on an opposite side thereof. The heat transfer unit is combined in the first opening of the light-transmitting shell. The heating element is combined with a lower side of the heat transfer unit. The light-emitting device is combined in the base and comprises an illuminator. The illuminator protrudes from the base. The base comprises a first hole, which communicates with the inside of the base. The rotating aurora reflector comprises a rotating shaft and at least one curved reflective sheet, and the at least one curved reflective sheet is combined on an upper side of the rotating shaft. The rotating shaft has a lower side thereof passing through the first hole of the base. The light-transmitting shell is combined above the base from the second opening side, and at the same time masking the rotating aurora reflector and the illuminator.

In this way, the light-emitting device and the heating element are used to combine a power supply unit. The heating element is used to heat the heat transfer unit. A container can be placed on the upper side of the heat transfer unit, which is used to place aromatic substances, such as solid aromatics, scented wax, essential oils or essential oils. The heat transfer unit conducts the heat source to the container to heat the aromatic substance to release the fragrance. Or the above-mentioned aromatic substances can be directly placed on the upper side of the heat transfer unit to directly heat the fragrance to release the fragrance. The illuminator of the light-emitting device is used to radiate a light source to the rotating aurora reflector, to reflect or diffuse reflection or some refraction to produce light similar to the aurora effect.

The illuminator of this light-emitting device comprises LED lamps. The light-emitting device can provide diffuse or light colors including northern lights or southern lights such as green or red. The rotating aurora reflector reflects or diffuses the omni-directional light of the light-emitting device to the tubular light-transmitting lampshade and the light-transmitting shell, which can produce a halo of soft light decoration, thereby producing aurora mood lighting decoration or lighting effects to match the above-mentioned fragrance atmosphere, which is different from the existing aroma diffuser lighting effects.

In some embodiments of the aroma diffuser of the present invention provided with an aurora-like situation, the aforementioned base also includes a rotating device mounted in the base and connected with the lower side of the rotating aurora reflector. The rotating device is used to rotate the rotating aurora reflector. The illuminator of the abovementioned light-emitting device provides a variety of imitated aurora colors. The light source illuminates the light reflected or diffusely reflected on the rotating curved reflective sheet. The color light source of the illuminator of the aforementioned light-emitting device radiates the rotating curved reflective sheets, and is reflected or diffusely reflected on the rotating curved reflective sheets as the rotating curved reflective sheets is rotating, so that the generated aurora arc or diffuse light alternately flickers or appears to further enhance the decorative effect of the aurora.

DETAILED DESCRIPTION OF THE PREFERRED EMBODIMENT

Figure 1:
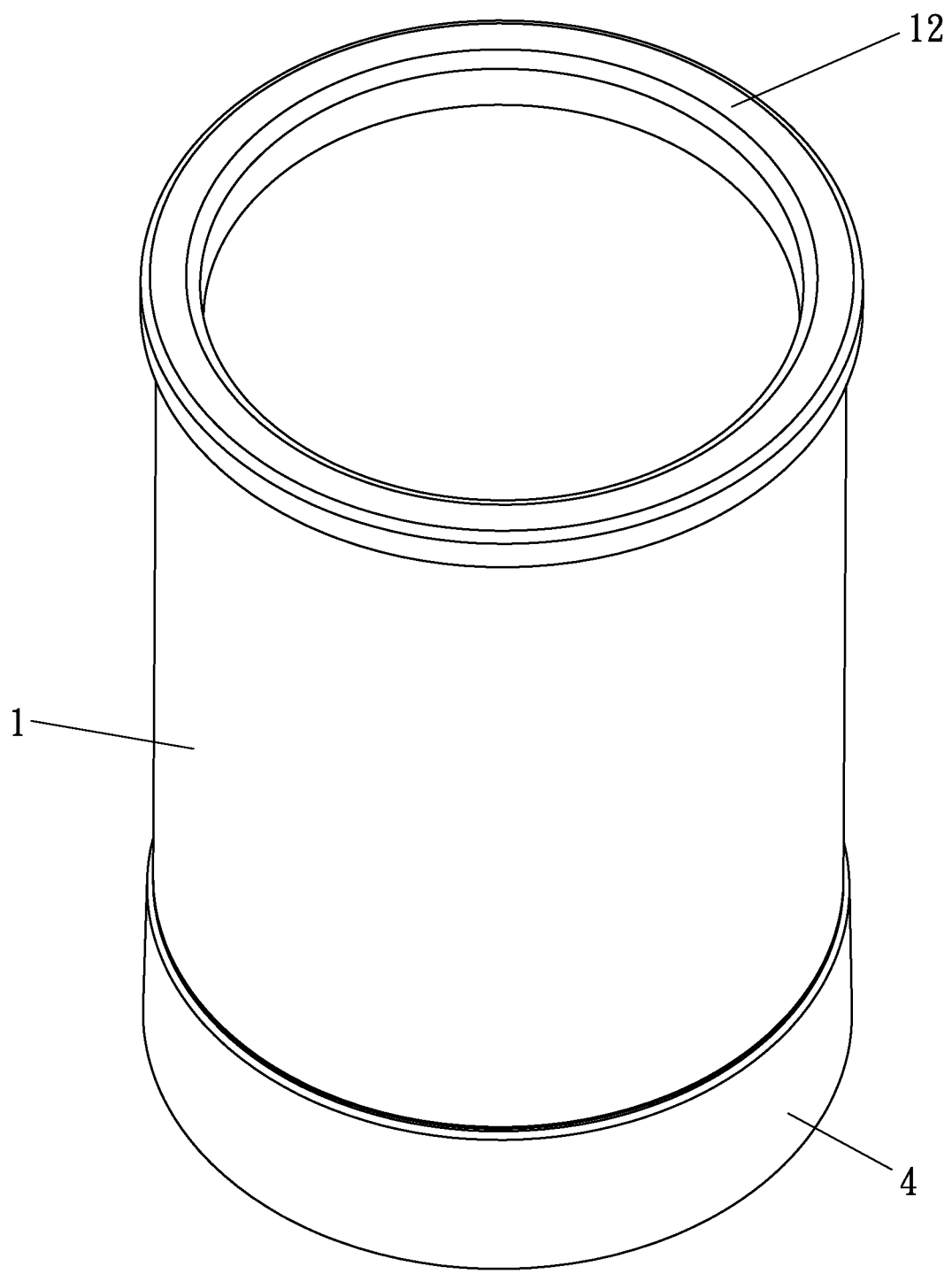
FIG. 1 is an elevational view of aroma diffuse simulating the aurora in accordance with the present invention.
Figure 2:
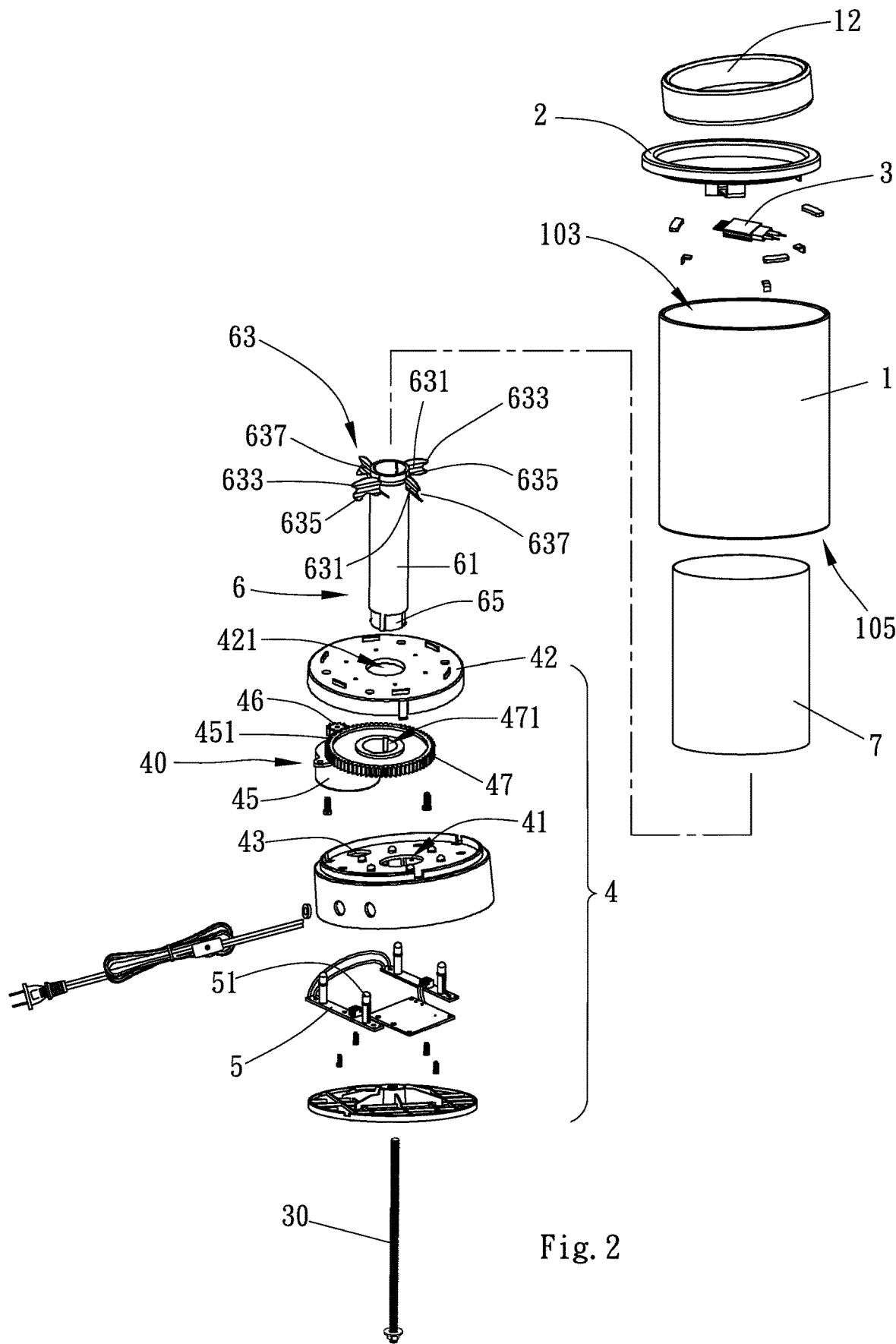
FIG. 2 is an exploded view of the aroma diffuse simulating the aurora in accordance with the present invention.
Figure 3:
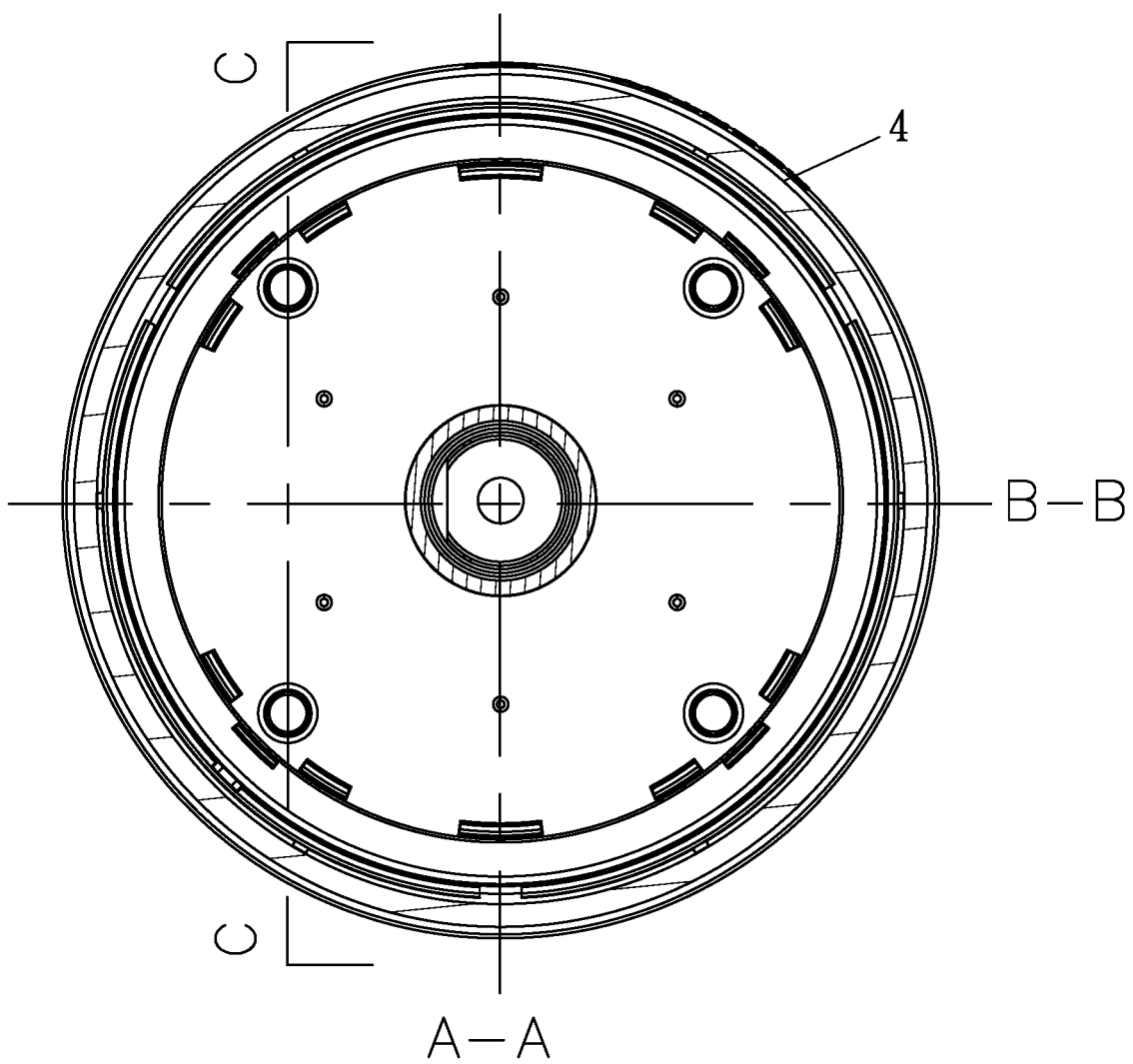
FIG. 3 is a bottom view of the aroma diffuse simulating the aurora in accordance with the present invention.
Figure 4:
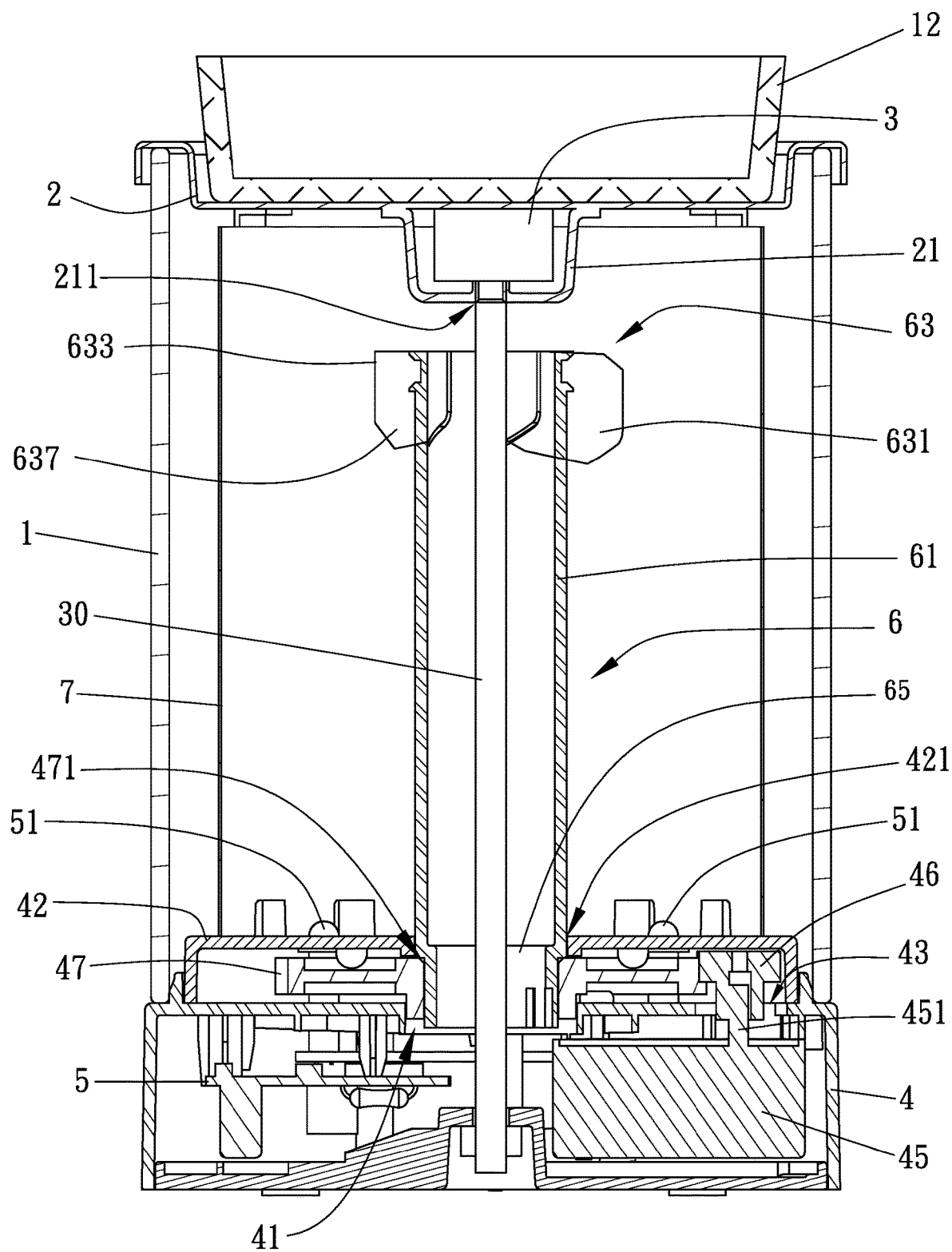
FIG. 4 is a sectional view taken along line A-A of FIG. 3.
Figure 5:
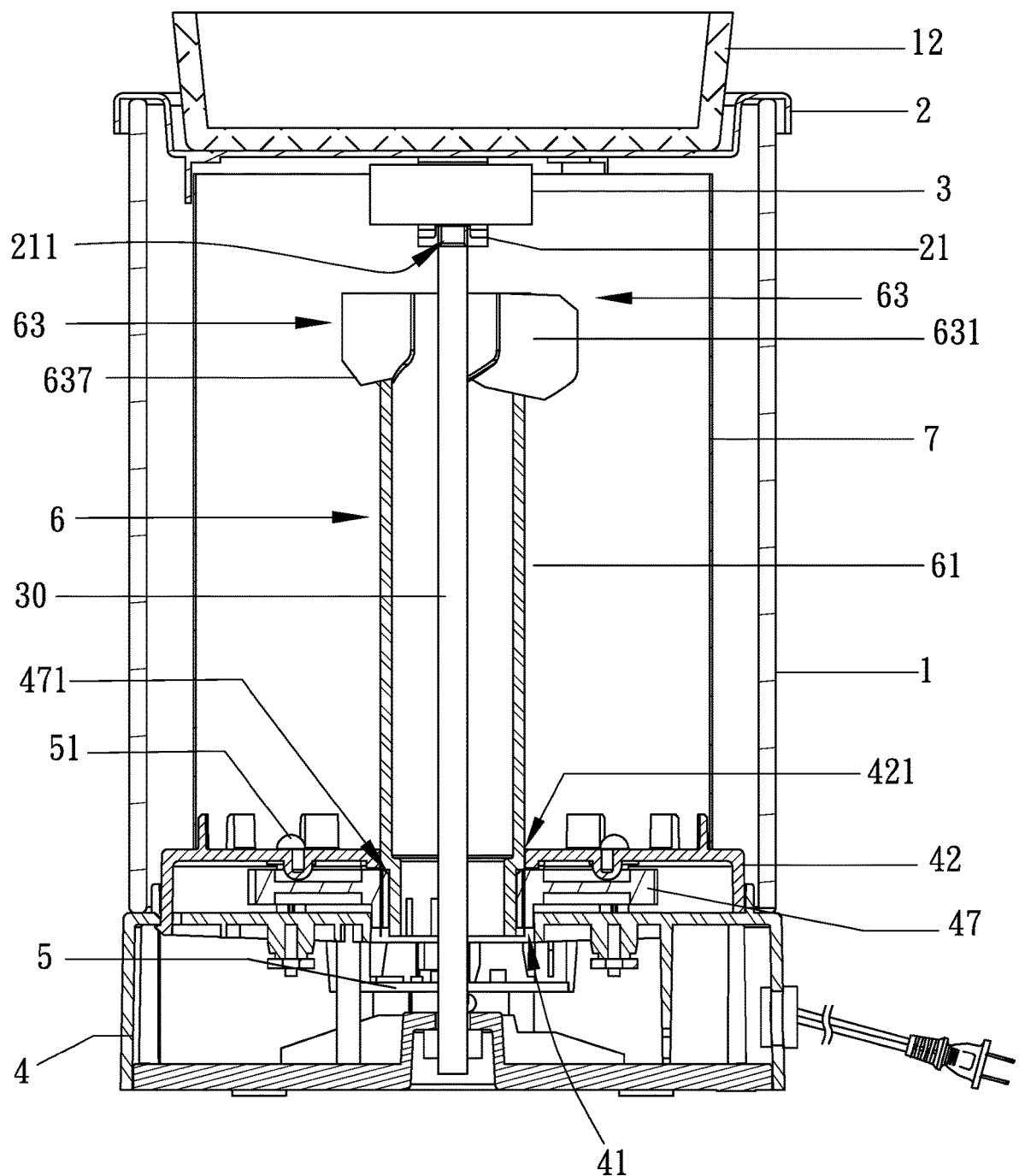
FIG. 5 is a sectional view taken along line B-B of FIG. 3.
Figure 6:
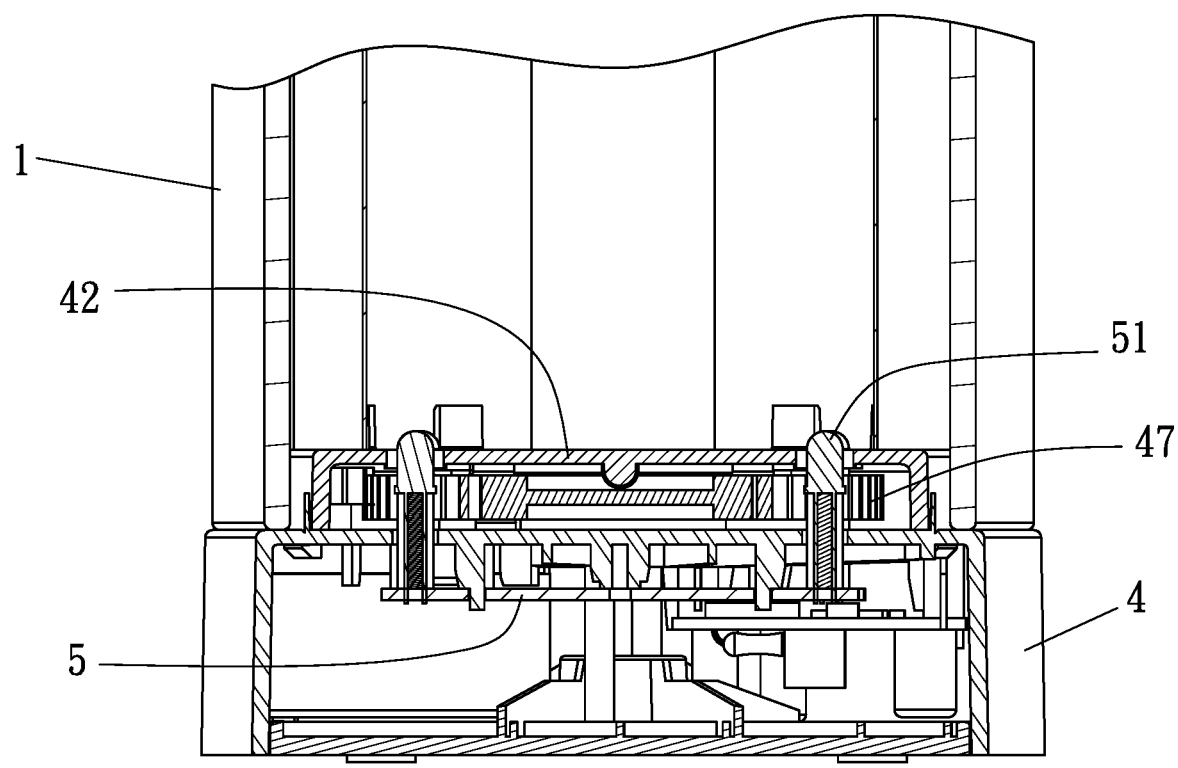
FIG. 6 is a sectional view taken along line C-C of FIG. 3.

Referring to FIGS. 1-6, an aroma diffuser simulating the aurora in accordance with the present invention is shown. The aroma diffuser comprises a light-transmitting shell 1, a heat transfer unit 2, a heating element 3, a base 4, a light-emitting device 5, and a rotating aurora reflector 6.

The light-transmitting shell 1 is a hollow shell in this embodiment. The light-transmitting shell 1 comprises a first opening 103 and a second opening 105. The first opening 103 is provided on one side of the light-transmitting shell 1, and the second opening 105 is provided on the other side of the light-transmitting shell 1. The heat transfer unit 2 is combined in the first opening 103 of the light-transmitting shell 1. The heating element 3 is combined with the lower side of the heat transfer unit 2. The light-emitting device 5 comprises an illuminator 51. The base 4 comprises a first hole 41, which communicates with the inside of the base 4. The light-emitting device 5 is combined in the base 4, and the illuminator 51 protrudes from the base 4. The rotating aurora reflector 6 comprises a rotating shaft 61, and at least one curved reflective sheet 63, and the curved reflective sheet 63 is combined on the upper side of the rotating shaft 61. The lower side 65 of the rotating shaft 61 passes through the first hole 41 of the base 4. The light-transmitting shell 1 is combined above the base 4 from the side of the second opening 105, and at the same time masks the rotating aurora reflector 6 and the illuminator 51.

In this way, the light-emitting device 5 and the heating element 3 are used to combine a power supply unit such as AC (not shown). The heating element 3 is used to heat the heat transfer unit 2. A container 12 can be placed on the upper side of the heat transfer unit 2, and the container 12 is used to place aromatic substances, such as solid aromatics, scented wax, essential oils, etc. The heat transfer unit 2 conducts the heat source to the container 12 to heat the aromatic substance to release the fragrance. Or the abovementioned aromatic substance can be directly placed on the upper side of the heat transfer unit 2 to directly heat the aromatic substance to release the fragrance, and in the embodiment, the aromatic substance is scented wax. The illuminator 51 of the light-emitting device 5 is used to radiate the light source to the rotating aurora reflector 6, to reflect or diffuse reflection or some refraction to produce light similar to the aurora effect.

The light-emitting device 5 comprises a LED lamp and a voltage transformation device, which can convert alternating current AC to DC power to provide LED use. The lightemitting device 5 can provide diffuse or light colors of northern lights or southern lights including green, red, or mixed yellow or pink. The rotating aurora reflector 6 reflective or diffuse the omni-directional light emitted by the light-emitting device to the light-transmitting shell 1, so as to produce aurora mood lighting decoration or lighting effects to match the above-mentioned fragrance atmosphere.

The illuminator 51 of the light-emitting device 5 includes, but is not limited to, LED lights, colored bulbs or various bulbs. In the embodiment, it is the LED lamp 51, and the LED chip can emit light radiation in all directions to illuminate the curved reflective sheet 63.

Please refer to FIGS. 2-5, which is an embodiment of the aroma diffuser provided with an aurora-like situation of the present invention. The curved reflective sheet 63 has an arc convex smooth surface 631 on one side. The material of the curved reflective sheet 63 is such as plastic, metal or glass. The arc convex smooth surface 631 includes polishing on these materials as a smooth surface, or an electroplated metal with a smooth surface mirror effect, which is electroplated nickel in the embodiment. The arc convex smooth surface 631 is electroplated with nickel metal on its surface to form a mirror structure to reflect light. The illuminator 51 illuminates the arc convex smooth surface 631 to produce a specular reflection effect. When part of the parallel light of the LED lamp touches the arc convex smooth surface 631, specular reflection occurs, and at least part of the reflected light is a parallel auroral arc effect, and a part is an arc light effect that is not completely parallel.

Please refer to FIGS. 2-5, which is an embodiment of the aroma diffuser provided with an aurora-like situation of the present invention. The arc convex smooth surface 631 of the curved reflective sheet 63 forms a crease concave surface 637 on the opposite side, and the free ends of the arc convex smooth surface 631 and the crease concave surface 637 are formed with a first arc-extending tail fin 633 and a second arc-extending tail fin 635. The illuminator 51 light irradiates the crease concave surface 637 to form a rough surface diffused aurora effect, combined with diffuse light spots such as radiant green, red, pink or yellow mixed colors, the aforementioned aurora arc is combined with the aurora situation effect. The light reflected by the first arc-extending tail fin 633 and the second arc-extending tail fin 635 produces a radiant auroral effect similar to parallel rays or arcs.

Please refer to FIGS. 2-5, which is an embodiment of the aroma diffuser provided with an aurora-like situation of the present invention. There are multiple curved reflective sheets 63, and the multiple curved reflective sheets 63 are arranged on the upper side of the rotating shaft 61 at intervals, so that the aforementioned aurora effect is significant.

Referring to FIGS. 1 to 5, it is an embodiment of an aroma diffuser with imitating aurora situation for this utility model. There are four curved reflective sheets 63 arranged in intervals on the upper side of the rotating shaft 61, and the four curved reflective sheets 63 are spaced apart, so that the light source of the illuminator 51 below the cylindrical light-transmitting shell 1 is radiated upwards, without blocking objects in the middle. The reflected or diffused rays of the curved reflective sheets 63 radiate downward in the light-transmitting shell 1 and there is no obstruction, and the arc-shaped or diffused radiant rays are generated to simulate the aforementioned auroral effect.

Refer to FIGS. 2-5, which is an embodiment of the aroma diffuser provided with the imitating aurora situation of the present invention. The arc convex smooth surfaces 631 of the curved reflective sheets 63 and the create concave surfaces 637 are arranged on the upper side of the rotating shaft 61 at intervals in the horizontal axis direction. The first arc-extending tail fin 633 and second arc-extending tail fin 635 form an up-and-down parallel configuration structure to reflect the light radiated upward from the lower side illuminator inside the light-transmitting shell 1, and produce arc-shaped or diffused radiation, and the arc-shaped or diffused radiation that simulates the aforementioned auroral effect is more significant.

Refer to FIGS. 1-6, which is an embodiment of the aroma diffuser provided with an aurora-like situation of the present invention. The aroma diffuser also comprises a tubular light-transmitting lampshade 7, and the above-mentioned embodiments can incorporate the tubular light-transmitting lampshade 7 inside the light-transmitting shell 1. The bottom side of the tubular light-transmitting lampshade 7 is combined on the base 4, and the rotating aurora reflector 6 and the illuminator 51 are masked at the same time. The tubular light-transmitting lampshade 7 or light-transmitting shell 1 is selected from light-transmitting or semi-transmitting materials, such as plastic materials, glass, silicone and other light-transmitting materials. In the embodiment, the tubular light-transmitting lampshade 7 is preferably selected from light-transmitting plastic materials, and its surface can be provided with various patterns or text. The tubular light-transmitting lampshade 7 is combined inside the lighttransmitting shell 1 made of glass. The illuminator 51 of the light-emitting device 5 is located in the lower side inside the tubular light-transmitting lampshade 7 and radiates upwards without blocking objects in the middle. The reflected or diffused light of the curved reflective sheet 63 radiates downward in the tubular light-transmitting lampshade 7 without obstruction. The arc-shaped or diffuse radiant light is generated to simulate the aforementioned aurora, which is reflected in the tubular light-transmitting lampshade 7 pattern and its outer light-transmitting shell 1 to produce aurora mood lighting decoration or patterns to match the aforementioned fragrance and atmosphere effects.

Refer to FIGS. 2-6, which is an embodiment of the aroma diffuser of the present utility model that is provided with an aurora-like situation. The base 4 also comprises a rotating device 40, and the above-mentioned various embodiments can set the rotating device 40 inside the base 4, while the rotating device 40 is connected to the lower side 65 of the rotating aurora reflector 6. The rotating device 40 is used to rotate the rotating aurora reflector 6. The color light source of the illuminator 51 of the aforementioned light-emitting device radiates the rotating curved reflective sheets 63, and is reflected or diffusely reflected on the rotating curved reflective sheets 63 as the rotating curved reflective sheets 63 is rotating, so that the generated aurora arc or diffuse light alternately flickers or appears to further enhance the decorative effect of the aurora.

Refer to FIGS. 2-6, which is an embodiment of the aroma diffuser provided with the imitating aurora situation of the present invention. The aroma diffuser also comprises a gear cover 42, and the gear cover 42 has a second hole 421. The base 4 also comprises a third hole 43. The rotating device 40 also comprises a motor 45, a first gear 46, and a second gear 47. A connecting hole 471 is formed in the middle of the second gear 47, and the motor 45 comprises a linkage rod 451. In this way, the first gear 46 and the second gear 47 are meshed and arranged on the base 4. The gear cover 42 is combined above base 4 and covers the first gear 46 and the second gear 47. The lower side 65 of the rotating shaft 61 passes through the first hole 41 and is connected to the connecting hole 471 of the second gear 47. The motor 45 is located in the base 4. The linkage rod 451 penetrates the third hole 43 of the base 4. The free end of the linkage rod 451 of the motor 45 is connected to the first gear 46 to drive the second gear 47 to rotate the rotating shaft 61 and the curved reflective sheet 63.

Refer to FIGS. 2-6, which is an embodiment of the aroma diffuser provided with the imitating aurora situation of the present invention. The heat transfer unit 2 also comprises a screw hole frame 21 which is arranged on the bottom side of the heat transfer unit 2. The screw hole frame 21 has a fixing hole 211. The aroma diffuser also comprises a connecting unit 30. The heating element 3 abuts under the heat transfer unit 2. In the embodiment, the rotating shaft 61 is, for example, a hollow rotating shaft 61. One side of the connecting unit 30 passes through the hollow rotating shaft 61, and then passes through the second hole 421, the connecting hole 471 and the first hole 41 to be combined with the base 4. The other side of the connecting unit 30 penetrates into the fixing hole 211 of the screw hole frame 21 to abut the heating element 3. The connecting unit 30 is a screw or connecting rod in the embodiment. The heat transfer unit 2 is a round metal bowl, or a round metal sheet, so that the heat transfer unit 2 uniformly and stably transfers the heat source to the aromatic substance in the glass container 12 to generate fragrance.

The above-mentioned heat transfer unit 2 is a thermally conductive material, and the heat transfer unit 2 is selected from any one of metal, ceramic, glass, etc.

The above are only multiple embodiments of the present invention, and cannot be used to limit the scope of implementation of the present invention, that is, all simple equivalent changes and modifications made according to the claims of the present invention and the specification should still belong to the scope of protection of the present invention.

What the invention claimed is:

1. An aroma diffuser, comprising a light-transmitting shell, a heat transfer unit, a heating element, a base, a light-emitting device and a rotating aurora reflector, wherein said light-transmitting shell comprises a first opening located on one side thereof and a second opening located on an opposite side thereof; said heat transfer unit is combined in said first opening of said light-transmitting shell; said heating element is combined with a lower side of said heat transfer unit; said light-emitting device is combined in said base and comprises an illuminator, said illuminator protruding from said base; said base comprises a first hole, which communicates with the inside of said base; said rotating aurora reflector comprises a rotating shaft and at least one curved reflective sheet, and said at least one curved reflective sheet is combined on an upper side of said rotating shaft, said rotating shaft having a lower side thereof passing through said first hole of said base; said light-transmitting shell is combined above said base from said second opening side, and at the same time masking said rotating aurora reflector and said illuminator.

2. The aroma diffuser as claimed in claim 1, wherein each said curved reflective sheet comprises an arc convex smooth surface located on one side thereof.

3. The aroma diffuser as claimed in any of claim 2, further comprising a rotating device mounted inside said base and connected with a lower side of said rotating aurora reflector and used to rotate said rotating aurora reflector.

4. The aroma diffuser as claimed in claim 3, further comprising a gear cover, wherein said gear cover comprises a second hole; said base further comprises a third hole; said rotating device comprises a motor, a first gear and a second gear, said second gear comprising a connecting hole in the middle, said motor being mounted in said base and comprising a linkage rod, said linkage rod passing through said third hole of said base and having a free end thereof connected to said first gear, said first gear and said second gear being meshed together and arranged on said base; said gear cover is mounted on said base to cover said first gear and said second gear; the lower side of said rotating shaft passes through said first hole and is connected to said connecting hole of said second gear.

5. The aroma diffuser as claimed in claim 1, wherein each said curved reflective sheet also comprises a crease concave surface opposite to said arc convex smooth surface, said arc convex smooth surface and said crease concave surface of each said curved reflective sheet having a respective free end formed with a first arc-extending tail fin and a second arc-extending tail fin respectively.

6. The aroma diffuser as claimed in claim 5, wherein the said at least one curved reflective sheet is multiple, and said multiple curved reflective sheets are arranged on an opposing upper side of said rotating shaft at intervals.

7. The aroma diffuser as claimed in claim 6, wherein the number of said multiple curved reflective sheets is 4.

8. The aroma diffuser as claimed in claim 7, wherein said arc convex smooth surface and said create concave surface of each said curved reflective sheet are arranged on the upper side of said rotating shaft at intervals in the horizontal axis direction, and said first arc-extending tail fin and said second arc-extending tail fin form a Form an up-and-down parallel configuration structure.

9. The aroma diffuser as claimed in claim 8, wherein said light-emitting device further comprises at least one LED lamp.

10. The aroma diffuser as claimed in claim 9, further comprising a tubular light-transmitting lampshade combined inside said light-transmitting shell to mask said rotating aurora reflector and said illuminator, said tubular light-transmitting lampshade having a bottom side thereof combined with said base.

11. The aroma diffuser as claimed in any of claim 10, further comprising a rotating device mounted inside said base and connected with a lower side of said rotating aurora reflector and used to rotate said rotating aurora reflector.

12. The aroma diffuser as claimed in claim 11, further comprising a gear cover, wherein said gear cover comprises a second hole; said base further comprises a third hole; said rotating device comprises a motor, a first gear and a second gear, said second gear comprising a connecting hole in the middle, said motor being mounted in said base and comprising a linkage rod, said linkage rod passing through said third hole of said base and having a free end thereof connected to said first gear, said first gear and said second gear being meshed together and arranged on said base; said gear cover is mounted on said base to cover said first gear and said second gear; the lower side of said rotating shaft passes through said first hole and is connected to said connecting hole of said second gear.

13. The aroma diffuser as claimed in any of claim 6, further comprising a rotating device mounted inside said base and connected with a lower side of said rotating aurora reflector and used to rotate said rotating aurora reflector.

14. The aroma diffuser as claimed in claim 13, further comprising a gear cover, wherein said gear cover comprises a second hole; said base further comprises a third hole; said rotating device comprises a motor, a first gear and a second gear, said second gear comprising a connecting hole in the middle, said motor being mounted in said base and comprising a linkage rod, said linkage rod passing through said third hole of said base and having a free end thereof connected to said first gear, said first gear and said second gear being meshed together and arranged on said base; said gear cover is mounted on said base to cover said first gear and said second gear; the lower side of said rotating shaft passes through said first hole and is connected to said connecting hole of said second gear.

15. The aroma diffuser as claimed in any of claim 8, further comprising a rotating device mounted inside said base and connected with a lower side of said rotating aurora reflector and used to rotate said rotating aurora reflector.

16. The aroma diffuser as claimed in claim 15, further comprising a gear cover, wherein said gear cover comprises a second hole; said base further comprises a third hole; said rotating device comprises a motor, a first gear and a second gear, said second gear comprising a connecting hole in the middle, said motor being mounted in said base and comprising a linkage rod, said linkage rod passing through said third hole of said base and having a free end thereof connected to said first gear, said first gear and said second gear being meshed together and arranged on said base; said gear cover is mounted on said base to cover said first gear and said second gear; the lower side of said rotating shaft passes through said first hole and is connected to said connecting hole of said second gear.

17. The aroma diffuser as claimed in any of claim 5, further comprising a rotating device mounted inside said base and connected with a lower side of said rotating aurora reflector and used to rotate said rotating aurora reflector.

18. The aroma diffuser as claimed in claim 17, further comprising a gear cover, wherein said gear cover comprises a second hole; said base further comprises a third hole; said rotating device comprises a motor, a first gear and a second gear, said second gear comprising a connecting hole in the middle, said motor being mounted in said base and comprising a linkage rod, said linkage rod passing through said third hole of said base and having a free end thereof connected to said first gear, said first gear and said second gear being meshed together and arranged on said base; said gear cover is mounted on said base to cover said first gear and said second gear; the lower side of said rotating shaft passes through said first hole and is connected to said connecting hole of said second gear.

19. The aroma diffuser as claimed in any of claim 1, further comprising a rotating device mounted inside said base and connected with a lower side of said rotating aurora reflector and used to rotate said rotating aurora reflector.

20. The aroma diffuser as claimed in claim 19, further comprising a gear cover, wherein said gear cover comprises a second hole; said base further comprises a third hole; said rotating device comprises a motor, a first gear and a second gear, said second gear comprising a connecting hole in the middle, said motor being mounted in said base and comprising a linkage rod, said linkage rod passing through said third hole of said base and having a free end thereof connected to said first gear, said first gear and said second gear being meshed together and arranged on said base; said gear cover is mounted on said base to cover said first gear and said second gear; the lower side of said rotating shaft passes through said first hole and is connected to said connecting hole of said second gear.

* * * * *